(12) United States Patent
Pizzini (10) Patent No.: US 9,522,078 B2
(45) Date of Patent: Dec. 20, 2016

(54) PATIENT POSITIONING SYSTEM AND METHOD FOR POSITIONING A PATIENT DURING A SURGICAL PROCEDURE

(75) Inventor: Mark-Alan D. Pizzini, Wynnewood, PA (US)

(73) Assignee: FOX CHASE CANCER CENTER, Jenkintown, PA (US)

( * ) Notice: Subject to any disclaimer, the term of this patent is extended or adjusted under 35 U.S.C. 154(b) by 192 days.

(21) Appl. No.: 12/669,397

(22) PCT Filed: Jul. 21, 2008

(86) PCT No.: PCT/US2008/070603
§ 371 (c)(1),
(2), (4) Date: May 13, 2010

(87) PCT Pub. No.: WO2009/015070
PCT Pub. Date: Jan. 29, 2009

(65) Prior Publication Data
US 2010/0288286 A1 Nov. 18, 2010

Related U.S. Application Data

(60) Provisional application No. 60/961,302, filed on Jul. 20, 2007.

(51) Int. Cl.
*A61G 13/12* (2006.01)
*A61F 5/37* (2006.01)
*A61G 13/10* (2006.01)

(52) U.S. Cl.
CPC ............. *A61F 5/3776* (2013.01); *A61G 13/10* (2013.01)

(58) Field of Classification Search
USPC ........ 600/227, 229; 128/845, 846, 849, 869, 128/96.1, 99.1, 100.1, 106.1, 107.1, 128/112.1; 602/19
See application file for complete search history.

(56) References Cited

U.S. PATENT DOCUMENTS

| | | | | |
|---|---|---|---|---|
| 4,132,229 A | * | 1/1979 | Morrison | 128/876 |
| 4,926,884 A | * | 5/1990 | Lonardo | 128/892 |
| 5,709,220 A | | 1/1998 | Kellan | |
| 5,728,047 A | * | 3/1998 | Edoga | 600/227 |
| 5,778,887 A | * | 7/1998 | Curtiss | 128/845 |
| 5,953,749 A | * | 9/1999 | Backs | 2/1 |
| 7,201,747 B2 | | 4/2007 | Edoga et al. | |
| 2007/0235042 A1 | * | 10/2007 | Vanderkam | 128/876 |
| 2011/0214677 A1 | * | 9/2011 | Snow | 128/845 |

* cited by examiner

*Primary Examiner* — Ophelia A Hawthorne
(74) *Attorney, Agent, or Firm* — Stephen H. Eland; Dann, Dorfman, Herrell & Skillman

(57) ABSTRACT

An apparatus and method are provided for positioning a patient on a surgical platform. The apparatus includes an elongated flexible web and a plurality of extension straps for connecting the apparatus to the surgical platform. Each extension strap includes a connector configured for connecting the apparatus to the platform. Adjustment mechanisms allow the extension straps to be adjusted to vary the tension in the web. The medical professional selects the desired position and orientation of the patient on the surgical platform and manipulates the patient into the desired position and orientation. A retention device is connected to a surgical platform and placed over the patient at the appropriate portion of the patient. A second end of the retention device is connected to a second side of the surgical platform. The retention device is then adjusted to increase the tension in the retention device.

25 Claims, 5 Drawing Sheets

PATIENT POSITIONING SYSTEM AND METHOD FOR POSITIONING A PATIENT DURING A SURGICAL PROCEDURE

PRIORITY CLAIM

This application is a 371 application of International Application No. PCT/US2008/070603 filed Jul. 21, 2008, claims priority to U.S. Provisional Patent Application No. 60/961,302, filed Jul. 20, 2007, the complete disclosure of each of the foregoing applications is hereby incorporated herein by reference.

FIELD OF THE INVENTION

The present invention relates to a system for positioning a patient during a surgical procedure. In particular, the present invention relates to a system for positioning and restraining a patient so that the patient can be positioned and maintained in a desired position and orientation during a surgical procedure.

BACKGROUND

During a surgical procedure it may be necessary to maintain a patient in a particular orientation. However, since the patient is typically unconscious, the patient cannot assist. Further still, even if the patient is conscious, the patient may not be able to maintain the proper positioning during a procedure.

The proper positioning of a patient becomes even more important in procedures such as laparoscopic surgery or robotic surgery. During such procedures is important to maintain the patient in a particular orientation and position. Unfortunately, according to standard operating procedures, the patient is restrained to the table or bed by taping the patient down. The tape is normally wrapped around the patient at several locations to ensure that the patient does not move during the procedure. However, if the surgeon decides that the patient needs to be moved, the patient much be untapped, re-positioned and then re-taped. All of this is cumbersome and time consuming.

A further problem with the existing procedure is that the tape residue on the table or bed readily attracts dirt and contaminants. Additionally, the tape used to hold the patient in place can leave a rash or skin irritation for the patient that can cause additional discomfort to the patient after the surgical procedure.

Although the use of tape has numerous disadvantages, it does have the advantage of being readily disposable to avoid cross-contamination between patients. Additionally, since the tape is on a roll, the amount of tape can be easily varied to accommodate patients of different size.

SUMMARY OF THE INVENTION

As can be seen from the foregoing, there exists a need for a system that can be utilized to properly position and restrain a patient during a surgical procedure. In light of this long-standing need, the present invention provides such a system.

In accordance with one aspect of the invention, an apparatus is provided for positioning a patient on a surgical platform. The apparatus includes an elongated flexible web and a plurality of extension straps extending from ends of the web. A plurality of adjustment mechanisms connect the straps to the web and are operable to adjust the length of the extension straps. A connector connected to the distal end of each strap is configured to attach each extension strap to the surgical platform. Additionally, the apparatus may include a patient engagement element connected with the web. The patient engagement element may be releasably attached to the web so it can be disposed after a procedure, and it may be formed of a material so that the element molds to the contour of the patient during use.

According to another aspect of the present invention, a method if provided for positioning a patient in a desired orientation during a procedure. The method includes the step of manipulating a patient into a desired orientation on a surgical platform. An elongated flexible positioning device is placed over the patient. A first end of the positioning device is connected to a first side of the platform and a second end of the positioning device is connected with a second side of the platform. The positioning device is then adjusted to increase the tension in the positioning device. A surgical procedure is then performed on the patient while the patient is retained by the device. After the procedure, the positioning device is re-adjusted to decrease the tension in the device.

DESCRIPTION OF THE DRAWINGS

The foregoing summary and the following detailed description of the preferred embodiments of the present invention will be best understood when read in conjunction with the appended drawings, in which.

DETAILED DESCRIPTION OF THE INVENTION

Figure 1:
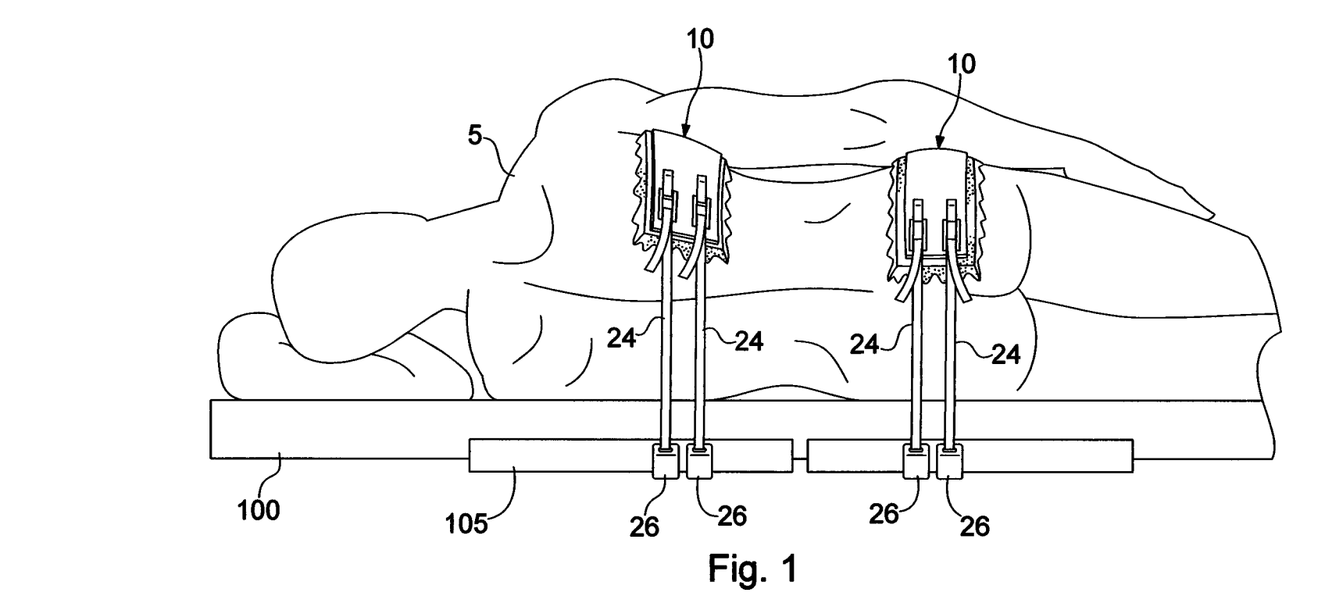
FIG. 1 is a side view of a patient positioning system being used to position a patient on a surgical table.

Referring now to FIGS. 1-5 generally and to FIG. 1 specifically, a patient positioning system is generally designated 10. The positioning system is used to position and maintain a patient 5 on a surgical table 100. As shown in FIG. 1, in certain instances it may be desirable to use multiple positioning elements to maintain the patient in the proper position.

Figure 2:
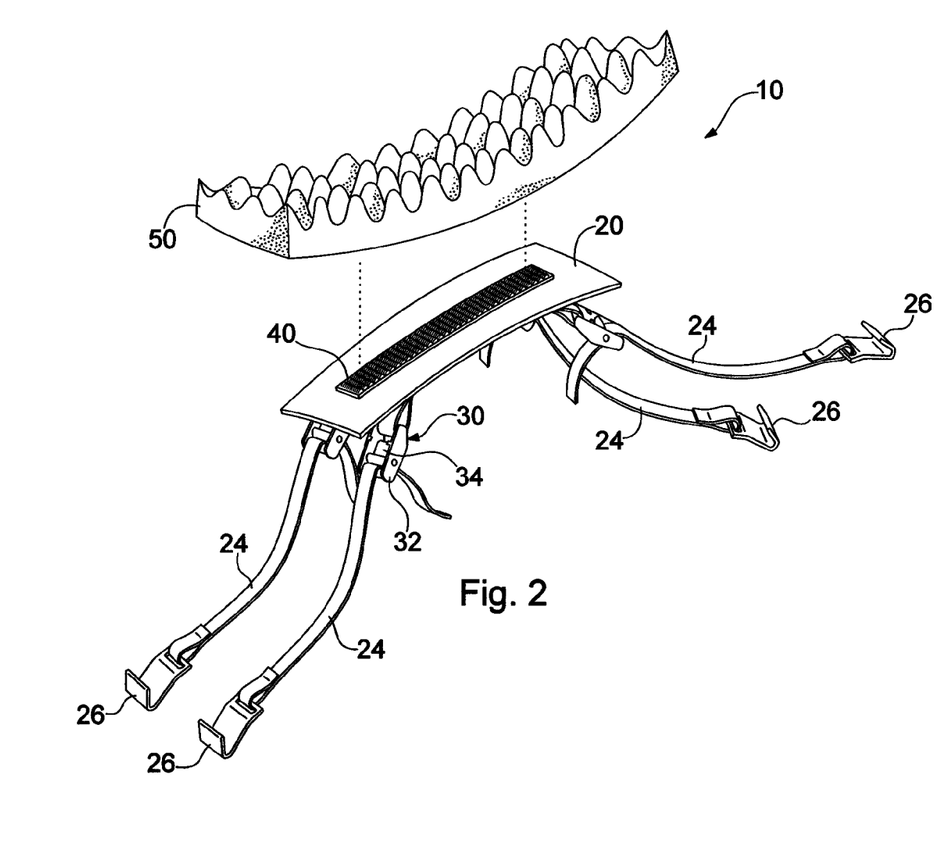
FIG. 2 is an exploded perspective view of the patient positioning system illustrated in FIG. 1.
Figure 3:
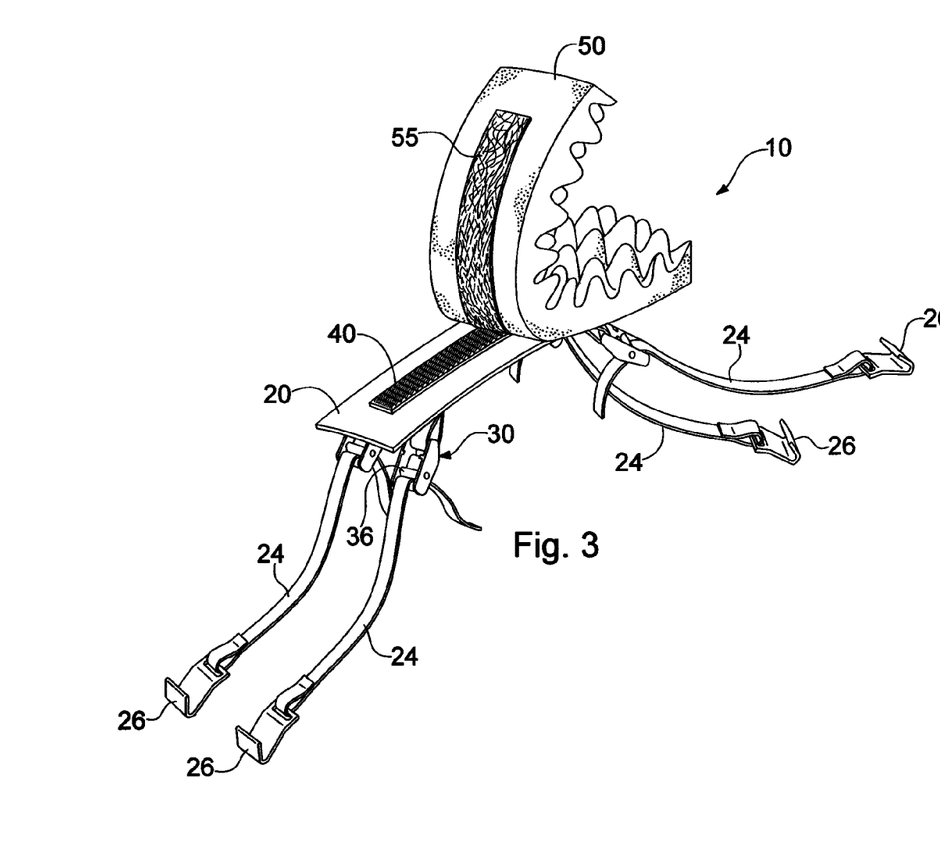
FIG. 3 is a perspective view of the patient positioning system illustrated in FIG. 2 shown with a patient engagement layer partially removed.

Referring now to FIG. 2, the patient positioning system 10 includes an elongated web 20, and a plurality of extensions 24. At the end of each extension is a connector 26 for connecting the extension to a surgical table or bed 100. The patient positioning system 10 may also include a disposable patient engagement element 50 that is removably connectable with the web. In this way, after a procedure, the patient engagement element 50 can be disposed to prevent cross-contamination with a subsequent patient.

The elongated web 20 is a generally planar element having a high tensile strength. The web is formed of a material that is flexible and does not degrade upon exposure to water or cleaning solutions that may be used to periodically clean the device 10. In the present instance, the web 20 is a 4" wide web of high strength nylon web. However, other suitable materials may include polyester webbing, polypropylene webbing or cotton webbing.

A plurality of extension adjustment mechanisms 30 are connected to the web 20. In the present instance, two adjustment mechanisms 30 are connected to each end of the web 20. However, as discussed further below, the number of adjustment mechanisms 30 may vary depending on the application.

Figure 4:
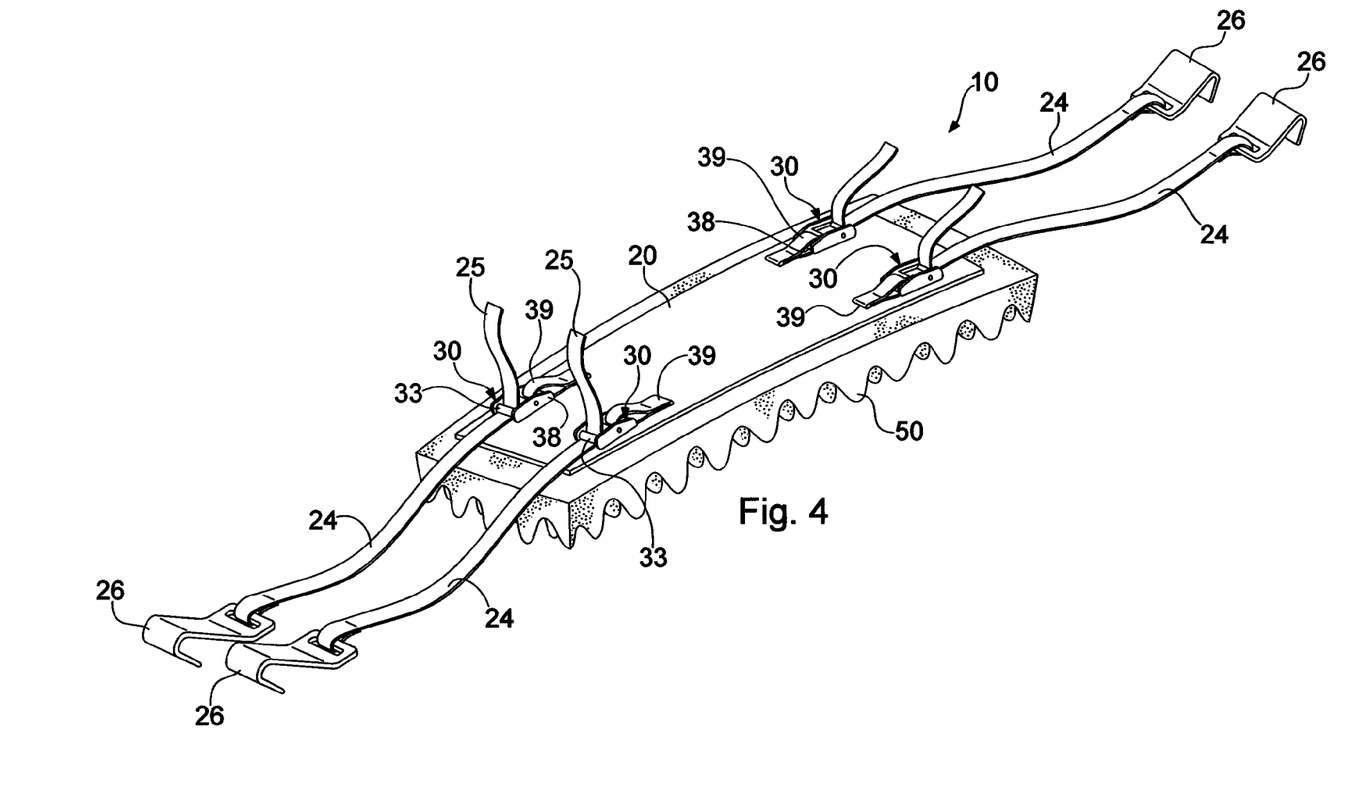
FIG. 4 is a perspective view of the patient positioning system illustrated in FIG. 2 viewed from the top of the system.
Figure 5:
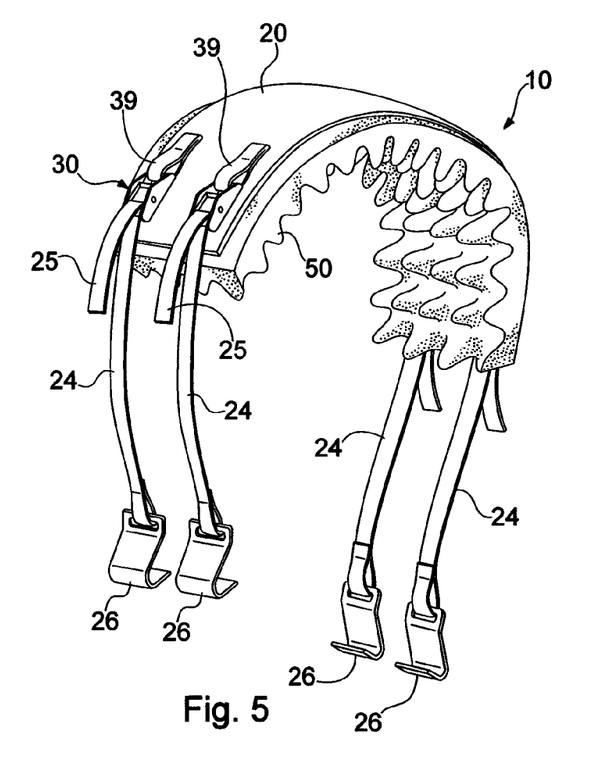
FIG. 5 is a perspective view of the patient positioning system illustrated in FIG. 4, in a curved orientation.

Each adjustment mechanism 30 is connected to the web 20 adjacent an end of the web. For example, as shown in FIG. 4, two adjustment mechanisms may be connected to each end of the web. Further, in the present instance, the two adjustment mechanisms at an end are spaced apart from one another. Specifically, in the present instance, each adjustment mechanism is adjacent one of the edges of the web. For example, as shown in FIG. 4, a first adjustment mechanism 30 is positioned near a first end of the web, adjacent the left edge of the web; the second adjustment mechanism is position near the first end adjacent the right edge of the web.

The adjustment mechanisms 30 may be one of a variety of elements for engaging and adjusting the extension straps 26. In the present instance, the adjustment mechanism 30 comprises a cam lock buckle, which includes a pivoting cam arm 34 mounted in a buckle 32. The pivoting cam arm 34 may include a plurality of teeth or gripping elements 36 for frictionally engaging one of the extension straps 26.

The adjustment mechanisms 30 are fixedly connected to the web. For instance, as shown in FIG. 4, each cam lock buckle 32 includes a mounting post 38. A connector strap 39 fixedly connected to the web 20 forms a loop that extends around the mounting post to retain the buckle 32 on the web. The connector strap 39 may be fixedly connected to the web in a variety of ways, such as by thermal or adhesive bonding. In the present instance, the connector strap is sewn onto the web. Specifically, a first end of the connector strap 38 is sewn to the web. The free end of strap 38 is then inserted into the buckle around the connecting post. The free end of the strap is then sewn down to the web to fix the buckle in position.

As shown in FIG. 4, each adjustment mechanism 30 is positioned adjacent an end of the web. In the figures, the adjustment mechanisms are illustrated spaced apart from the ends of the web a distance that is about equal to the length of the buckle. However, it may be desirable to mount the adjustment mechanisms closer to the ends of the web.

Each of the adjustment mechanisms is configured to cooperate with one of the extension straps 26. The extension straps are narrow straps that are also formed of a flexible, high tensile strength material that does not degrade upon exposure to water. The materials for the extension straps are similar to those discussed above in connection with the web 20. In the present instance, each extension 24 has a width that is narrower than the width of the web 20. For instance, in the present instance, each extension 24 has a width of approximately 1".

As discussed above, each extension 26 engages one of the adjustment mechanisms 30. For instance, in the present instance, a free end of the extension strap 24 is threaded into the buckle 32, under the locking arm and around a crossbar 33. The locking arm 34 pivots into engagement with the strap to pinch the web against the crossbar 33 of the buckle.

The locking arm 34 of the adjustment mechanism is configured to allow the length of the extension strap to be shortened by simply pulling on the free end 25 of the strap. However, in order to elongated the strap (i.e. reduce the length of the free end 25), the locking arm is pivoted out of the way. In this way, the length of the strap can be readily adjusted with a single hand. However, the adjustment mechanism does not readily allow the strap to be extended, thereby providing a safety against inadvertently loosening the patient during a procedure, which could lead to an undesired or inadvertent movement of the patient during a procedure.

Each extension strap 24 includes a connector 26 for connecting the extension strap to the platform that the patient rests upon. The connector 26 is fixedly connected to the end of the strap remote from the adjustment mechanism 30. For instance, in the present instance, the end of the extension strap passes through a slot in the body of the connector 26. The end of the extension strap is then sewn back onto the extension strap to form a closed loop entraining the connector 26.

Each connector 26 is an open connector for readily attaching the extension straps to the surgical platform 100. For instance, as shown in FIGS. 2-5, each connector forms a generally U-shaped channel having an opening that progressively narrows from the opening of the channel to the base. Similarly, the connectors could be formed in the shape of a hook or other configuration that can hook onto a rail or frame 105 of the surgical platform 100. Additionally, the connectors may include a latch or other element to retain the connector on the rail of the surgical platform. By incorporating a latch, the connector is not readily removable from the rail without disengaging the latch to allow the connector to be removed. However, in the present instance, the connectors do not include a latch so that the connectors are readily removable after a procedure by simply removing the tension in the extension straps.

During a procedure it is anticipated that biological fluids from the patient 5 may come into contact with the device 10. Therefore, to prevent cross contamination, the system may be configured as a single use system. However, in the present instance, the system is designed to be a multiple use device. To prevent cross-contamination, the device 10 includes a disposable element releasably connected with the web 20. The disposable element is designed to be the portion of the device that comes into contact with the patient.

The patient engagement element 50 may be a simple liner, such as an absorbent liner that is removably connected with the web, such as by a releasable adhesive. However, in the present instance, the patient engagement element 50 is an elongated pad. Specifically, the engagement element is a resiliently deformable pad having a thickness that is at least 20 times as thick as the thickness of the web. The patient engagement element may be formed of a number of different materials. In the present instance, the patient engagement element is formed of a resilient pad, such as a foam pad. One exemplary type of foam is a polymer foam commonly referred to as egg crate foam.

The patient engagement element 50 is configured to overlie substantially the entire length of the web 20. Accordingly, in the present instance, the patient engagement element 50 is generally co-extensive with the web, and may overlap the edges of the web. In this way, fluids or other contaminants from the patient are likely to be absorbed into the patient engagement element 50, which is disposable, rather than the web 20.

As discussed above, in the present instance, the patient engagement element 50 is disposable. Therefore, in the present instance, the patient engagement element 50 is removably connected with the web 20. For example, referring to FIG. 3, a first connector 40, such as one half of a hook and loop connector, is fixedly connected to the top surface of the web 20. Similarly, a second connector 55, such as a second half of the hook and loop connector, is fixedly connected to the bottom face of the egg crate foam layer 50. In this way, prior to use, a disposable layer of foam 50 can be applied to the web 20 using the hook and loop connectors on the foam pad and the web. After the procedure, the foam 50 can be removed and discarded. Although the hook and loop are desirable connectors, other connectors may also be suitably employed. For instance, the patient engagement element 50 may by connected to the web using a releasable adhesive.

Method of Use

Configured as discussed above, the patient positioning system 10 is operable as follows. The patient 5 is placed onto the surgical platform 100, which may be a table or bed or other platform. The patient is manipulated into the desired position for the surgical procedure. For instance, referring to FIG. 1, the patient is manipulated so that the patient is laying on his side. Obviously, such a position is a relatively unstable position, and the patient could readily be moved toward a supine or prone position during the surgery.

Prior to the procedure, if a disposal patient engagement element 50 is to be used, the element is releasably attached to the web. After the patient is properly manipulated into the desired orientation, the patient position device 10 is placed over the patient and tightened. Specifically, the connectors 26 at the end of two of the extension straps are connected to a rail or frame member on one side of the platform. For instance, the connectors 26 are hooked onto a tubular rail 105 connected with the platform 100.

The connectors may be hooked onto the rail 105 so that the extension strap at the first end of the web are generally parallel, as shown in FIG. 1. However, it may be desirable to hook the connectors onto the rails so that the connectors are spaced further apart than the two corresponding buckles attached to the web. In this way, the extension straps at the first end are divergent after they are connected to the rail.

After the first two connectors are hooked onto one side of the platform 100, the device 10 is placed over the patient at the appropriate location. The device is placed over the patient so that the web overlies the patient. Further, if a patient engagement element 50 is incorporated, the engagement element overlies and engages the patient. After the device is placed over the patient, the connector 26 for the straps at the opposite end of the web are connected to a rail or frame member on an opposing side of the surgical platform. The extension straps may be extended as necessary to ensure that the device is sufficiently long to fit over the patient and connect to the opposite side of the surgical platform.

After the device is connected to the surgical platform, the position of the patient is checked and then the tension in the device is increased to apply a series of forces that tend to retain the patient in the desired position and orientation. Specifically, to increase the tension in the device, the free ends of the extension straps are shortened by pulling on the free end 25 of one or more of the extension straps. Each of the extension straps is independently operable, so each strap can be selectively manipulated to control the direction and amount of tension through each strap independently to alter the direction and orientation of the retention forces provide by the device during use.

Additionally, as shown in FIG. 1, in some applications, it is desirable to use a second device 10 at a second location to hold the patient down. In this way, a plurality of positioning device may be used at different points along the patient to retain the patient and/or the patient's limbs in the desired position and orientation.

As the tension in the device increases, the device pulls down on the patient. In the present instance, a foam layer is included as a patient engagement layer. Therefore, when the tension in the device increases, the device presses the foam layer firmly up against the patient. In this way, the foam resiliently deforms to mold into the shape of the patient to provide a custom form surface for retaining the patient.

During the surgical procedure, it may be desirable to tighten the straps to increase the tension applied to the belt to hold the patient. To do so, the medical personnel simply needs to selectively pull on the free end of the relevant extension straps. Additionally, if desired, the orientation of the patient may be altered during a procedure without the need to remove the positioning device 10.

Specifically, to move or re-orient a patient, the extension straps 24 are elongated by manipulating the locking arms 34 to disengage the straps from the buckles to allow the straps to be extended. After the device 10 is sufficiently elongated to move the patient, the patient is manipulated into the newly desired position, and the device is then retightened by selectively pulling on the free ends 25 of the extension straps.

After the procedure is completed, the extension straps are elongated to loosen the device. The connectors 26 are disconnected from a first side of the surgical platform and then disconnected from the second side of the surgical platform. If a disposable patient engagement element is used, the element is removed from the web and discarded.

It will be recognized by those skilled in the art that changes or modifications may be made to the above-described embodiments without departing from the broad inventive concepts of the invention. For instance, in the above description, the device 10 is described as including a pair of extension straps at each end. However, the number of connectors at each end may be varied. For instance, the device may include only a single extension strap at each end. Similarly, the device may include three or more extension straps at each end. Further, the width and length of the web may be modified for different applications. For example, in the instance of a pediatric procedure it may be desirable to use a narrower web 20. Such a narrower web may have only a single extension strap 24 and connector at each end. It should therefore be understood that this invention is not limited to the particular embodiments described herein, but is intended to include all changes and modifications that are within the scope and spirit of the invention as set forth in the claims.

The invention claimed is:

1. A patient positioning system, comprising:
   a surgical platform configured to support a patient during a surgical procedure, wherein the platform comprises a front side having a front rail and a back side having a back rail;
   an elongated flexible web having a central portion, a first end and a second end;
   a deformable pad connected to the web, wherein the deformable pad overlies a portion of the central portion;
   a first extension strap connected with the first end of the web;
   a second extension strap connected with the second end of the web;
   first and second adjustment mechanisms connecting the first and second extension straps to the web, wherein operating the adjustment mechanisms increases tension in the first and second extension straps while the deformable pad engages a patient;

a first connector connected to a distal end of the first extension strap, wherein the first connector comprises a generally open u-shaped connector configured to releasably connect the first extension strap to the front rail of the platform; and a second connector connected to a distal end of the second extension strap, wherein the second connector comprises a generally open u-shaped connector configured to releasably connect the second extension strap to the back rail of the platform;

wherein the first and second adjustment mechanisms are independently operable so the first and second extension straps can be selectively manipulated to control a direction and amount of tension through each extension strap independently to alter a direction and orientation of retention forces provided against the patient during a surgical procedure.

2. The patient positioning system of claim 1 wherein the first connector is connected to the front rail and the second connector is connected to the back rail.

3. The patient positioning system of claim 2 wherein the deformable pad is releasably connected with the elongated flexible web.

4. The patient positioning system of claim 3 wherein the deformable pad is resiliently deformable to mold to a contour of the patient.

5. The patient positioning system of claim 3 wherein the first and second extension straps are formed of a material having a higher tensile strength than the deformable pad.

6. The patient positioning system of claim 1 wherein the first and second adjustment mechanisms comprise one-way locking elements that allow the first and second extension straps to be readily shortened, but resist extension of the straps.

7. The apparatus of claim 1 wherein the deformable pad is a layer of polymer foam having a thickness that is at least 20 times the thickness of the web.

8. The apparatus of claim 1 wherein the first extension strap is generally aligned with second extension strap.

9. A method for positioning a patient in a desired orientation during a procedure, comprising the steps of:
placing a patient on a surgical platform having a first side and a second side;
manipulating the patient into a desired orientation;
placing a positioning device over the patient, wherein the positioning device has an elongated and flexible central portion covered by a resiliently deformable pad;
connecting a first end of the positioning device to the first side of the platform using a first connection strap and a second connection strap disposed at an angle to the first connection strap;
connecting a second end of the positioning device to the second side of the platform;
reducing a length of the first connection strap or second connection strap to increase a tension in the device to pull the deformable pad down against the patient to maintains the patient in a desired position and orientation during a surgical procedure;
performing a surgical procedure after the step of reducing the length of the first connection strap or second connection strap while the patient remains in the desired position;
changing the tension in the positioning device while the device remains engaged with the patient; and
increasing the length of the positioning device to decrease the tension in the device to decrease retentive force provided by the positioning device.

10. The method of claim 9 wherein the step of connecting comprises releasably attaching the deformable pad to the central portion.

11. The method of claim 10 wherein the deformable pad is formed of foam, and the step of reducing the length of the first connection strap or the second connection strap comprises decreasing the length of the first connection strap or the second connection strap to increase forces urging the foam against the patient, thereby deforming the foam into a shape conforming to the patient.

12. The method of claim 9 comprising the step of disconnecting one of the first end and the second end of the positioning device from the surgical platform.

13. The method of claim 9 wherein the step of connecting a first end of the positioning device to the first side of the surgical platform comprises connecting the first and second extension straps so that the first and second extension straps are divergent.

14. The method of claim 9 wherein the step of changing the tension comprises increasing tension in the positioning device without releasing the tension in the positioning device.

15. An apparatus for positioning a patient in a desired orientation on a surgical platform during a procedure, comprising:
a web, wherein the web comprises an elongated flexible webbing, wherein the web comprises a central portion;
a plurality of extension straps extending from the web, wherein first and second extension straps extend from a first end of the web and a third extension strap extends from a second end of the web;
adjustment mechanisms connecting the extension straps to the web, wherein the adjustment mechanisms are operable to adjust a length of the extension straps while the extension straps are tensioned;
a connector connected to a distal end of each extension strap, wherein the connector for each strap is configured to attach the extension straps to the surgical platform; and
a deformable pad releasably connected with the web that is deformable to mold to a contour of the patient when the extension straps are adjusted to tighten the extension straps to retain the patient in a desired position;
wherein each extension strap is independently operable, so each extension strap can be selectively manipulated to control a direction and amount of tension through each extension strap independently to alter a direction and orientation of retention forces provided against the patient by the device during a surgical procedure.

16. The apparatus of claim 15 wherein the deformable pad is releasably connectable with the web.

17. The apparatus of claim 16 wherein the deformable pad overhangs edges of the web.

18. The apparatus of claim 15 wherein the deformable pad is a layer of polymer foam having a thickness that is at least 20 times the thickness of the web.

19. An apparatus for positioning a patient in a desired orientation on a surgical platform during a procedure, comprising:
an elongated flexible web having a central portion, wherein the central portion is covered by a deformable pad;
a plurality of extension straps extending from the elongated flexible web, wherein first and second extension straps extend from a first end of the web and a third extension strap extends from a second end of the web;

adjustment mechanisms connected to the extension straps, wherein the adjustment mechanisms are operable to reduce a length of one of the extension straps to increase tension in the web;

a connector connected to a distal end of each extension strap, wherein the connector for each strap comprises a rail engagement shape for engaging a tube or rail connected to the surgical platform wherein each extension strap is independently operable, so each extension strap can be selectively manipulated to control a direction and amount of tension through each extension strap independently to alter a direction and orientation of retention forces provided against the patient by the device during a surgical procedure.

20. The apparatus of claim 15 comprising a first pad connector extending along a length of the web and a second pad connector extending along the pad wherein the first and second pad connectors releasably connect the pad with the web.

21. The apparatus of claim 19 wherein the deformable pad is a layer of polymer foam having a thickness that is at least 20 times the thickness of the web.

22. The apparatus of claim 15 wherein a first one of the adjustment mechanisms is connected adjacent a first edge of the web and a second one of the adjustment mechanisms is connected to a second edge of the web and aligned with the first adjustment mechanism so that a first one of the extension straps is aligned with a second one of the extension straps.

23. The apparatus of claim 22 wherein a third one of the adjustment mechanisms is connected adjacent the first edge of the web and a fourth one of the adjustment mechanisms is connected adjacent the second edge of the web and aligned with the third adjustment mechanism so that a third one of the extension straps is aligned with a fourth one of the extension straps.

24. The apparatus of claim 19 wherein the deformable pad comprises a resiliently deformable foam pad releasably connected to the central portion of the web.

25. The apparatus of claim 19 wherein the adjustment mechanisms are operable to selectively increase a length of the extension straps to thereby decrease tension in the web.

* * * * *